United States Patent
Benowitz (10) Patent No.: US 7,172,871 B1
(45) Date of Patent: Feb. 6, 2007

(54) METHODS AND COMPOSITIONS FOR MODULATING AXONAL OUTGROWTH OF CENTRAL NERVOUS SYSTEM NEURONS

(75) Inventor: Larry I. Benowitz, Newton Centre, MA (US)

(73) Assignee: Children's Medical Center Corporation, Boston, MA (US)

( * ) Notice: Subject to any disclaimer, the term of this patent is extended or adjusted under 35 U.S.C. 154(b) by 63 days.

(21) Appl. No.: 09/656,915

(22) Filed: Sep. 7, 2000

(51) Int. Cl.
*G01N 33/00* (2006.01)

(52) U.S. Cl. ............................ 435/7.1; 435/4; 435/375

(58) Field of Classification Search ................. 435/7.1
See application file for complete search history.

(56) References Cited

U.S. PATENT DOCUMENTS

| | | | | |
|---|---|---|---|---|
| 4,883,666 | A | 11/1989 | Sabel et al. ................. | 424/422 |
| 5,187,162 | A | 2/1993 | Marangos et al. ............ | 514/46 |
| 5,250,414 | A | 10/1993 | Schwab et al. ............. | 435/7.72 |
| 5,447,939 | A | 9/1995 | Glasky et al. .............. | 514/310 |
| 6,001,583 | A * | 12/1999 | Margolis ................... | 435/7.23 |

FOREIGN PATENT DOCUMENTS

| | | |
|---|---|---|
| WO | WO 94/00132 | 1/1994 |
| WO | WO 97/03652 | 2/1997 |
| WO | WO 99/11274 | 3/1999 |

OTHER PUBLICATIONS

The American Heritage® Dictionary of the English Language (2000) 4th Ed. by Houghton Mifflin Company.*
Bossemeyer (1995) "Protein Kinases-structure and function." FEBS Letters 369: 57-61.*
Kandel et al. (2000) Principles of Neural Science (4th Ed.) Chapter 13 "Modulation of Synaptic Transmission: Second Messengers" pp. 229-252.*
Adler et al. (Sep. 1996) "Effects of chemopreventive selenium compounds on Jun N-kinase activites." Carcinogenesis 17(9): 1849-54.*
Rowland-Gagne & Greene (Feb. 1990) "Multiple pathways of N-kinase activation in PC12 cells." J Neurochem. 54(2): 424-33.*
Benowitz et al. J Biol. Chem. 273(45):29626-29634, Nov. 6, 1998.*
Cheung and Minglin, Methods in Enzymology, vol. 38, 1974, pp. 223-239.*
Rowland-Gagné, et al., (1990), *Jour. of Neuro.*, vol. 54, No. 2, 424-433.
Volonté, Cinzia, (1993), *Neuro. Letters*, 159, 119-122.
Benowitz, L.I. et al. (1997) "Inosine stimulates axonal regeneration from goldfish retinal ganglion" *Dept. of Neurosci. Abstracts* 23 (1-2).
Bold, J.M. et al. (1985) "Central Effects Of Nicotinamide and Inosine Which Are Not Mediated Through Benzodiazepine Receptors" *Br. J. Pharmac.* 84:689-696.
Braumann, T. et al. (1986) "Fate of Cyclic Nucleotides in PC12 Cell Cultures: Uptake, Metabolism, and Effects of Metabolites On Nerve Growth Factor-Induced Neurite Outgrowth" *J. Neurochem.* 47(3):912-919.

Christjanson, L.J. et al. (1993) "Stimulation Of Astrocyte Proliferation By Purine And Pyrimidine Nucleotides And Nucleosides" *GLIA* 7:176-182.
Greene, L.A. et al. (1990) "Purine Analogs Inhibit Nerve Growth Factor-Promoted Neurite Outgrowth By Sympathetic And Sensory Neurons" *J. Neuroscience* 10(5):1479-1485.
Gysbers, John W., et al. (1992) "Guanosine enhances NGF-stimulated neurite outgrowth in PC12 cells" *NeuroReport* 3(11):997-1000.
Gysbers, John W., et al. (1996)"GTP and Guanosine Synergistically Enhance NGF-Induced Neurite Outgrowth From PC12 Cells" *Int. J. Devl Neuroscience* 14(1):19-34.
Hayashi, E. et al. (1978) "Effects Of Purine Compounds On Cholinergic Nerves, Specificity Of Adenosine and Related Compounds On Acetylcholine Release in Electrically Stimulated Guinea Pig Ileum" *Eur. J. Pharmacol.* 48:297-307.
Huffaker, T. et al. (1984) "Adenosine Inhibits Cell Division and Promotes Neurite Extension in PC12 Cells" *J. Cellular Physiol.* 120:188-196.
Juhász-Nagy, A. and D.M. Aviado (1977) "Inosine As A Cardiotonic Agent That Reverses Adrenergic Beta Blockade"0 *J. Pharmacol. & Exper. Therapeutics* 202(3):683-695.
Matz, H. and L. Hertz (1989) "Adenosine Metabolism in Neurons And Astrocytes In Primary Cultures" *J. Neurosci. Res.* 24:260-267.
Nagasawa, H. and K. Kogure (1991) "Alterations of [$^3$H]inositol 1,4,5-triphosphate Binding in the Postischemic Rat Brain" *Neuroscience Letters* 133:129-132.
Rathbone, M.P. et al. (1992) "Extracellular Purine Nucleosides Stimulate Cell Division and Morphogenesis: Pathological and Physiological Implications" *Medical Hypotheses* 37:232-240.
Rolls, E.T. et al. (1996) "Responses Of Neurons In The Primate Taste Cortex To The Glutamate Ion And To Inosine 5'-Monophosphate" *Physiol. & Behav.* 59(4/5):991-1000.
Satoh, T. et al. (1987) "Induction of Neurite Formation in PC12 Cells By Microinjection of Proto-Oncogenic Ha-*ras* Protein Preincubated With Guanosine-5'-O-(3-Thiotriphosphate)" *Mol. Cell Biol.* 7(12);4553-4556.

(Continued)

Primary Examiner—David S Romeo
Assistant Examiner—Daniel C Gamett
(74) Attorney, Agent, or Firm—Nixon Peabody, LLP (57) ABSTRACT

Methods and compositions for modulating the axonal outgrowth of central nervous system neurons are provided. Methods for stimulating the axonal outgrowth of central nervous system neurons following an injury (e.g., stroke, Traumatic Brain Injury, cerebral aneurism, spinal cord injury and the like) and methods for inhibiting the axonal outgrowth of central nervous system neurons in conditions such as epilepsy, e.g., posttraumatic epilepsy, and neuropathic pain syndrome, are also provided. These methods generally involve contacting the central nervous system neurons with a compound that modulates the activity of N-kinase, or analog thereof. The methods and compositions are particularly useful for modulating the axonal outgrowth of mammalian central nervous system neurons, such as mammalian cortical neurons or retinal ganglion cells. Pharmaceutical and packaged formulations that include the compounds of the invention that modulate the activity of N-kinase are also provided.

5 Claims, 2 Drawing Sheets

OTHER PUBLICATIONS

Schwalb, J.M. et al. (1996) "Optic Nerve Glia Secrete A Low-Molecular-Weight Factor That Stimulates Retinal Ganglion Cells To Regenerate Axons In Goldfish" *Neurosci.* 72(4):901-910.

Schwalb, J.M. et al. (1995) "Two Factors Secreted by the Goldfish Optic Nerve Induce Retinal Ganglion Cells to Regenerate Axons in Culture" *J. Neurosci.* 15(8):5514-5525.

Standaert, F.G. et al. (1976) "Effects of Cyclic Nucleotides On Mammalian Motor Nerve Terminals" *J. Pharmacol. & Exper. Therapeutics* 199(3):544-552.

Svensson, B. et al. (1993) "Detection of a Purine Analogue-Sensitive Kinase In Frog Sciatic Nerves-Possible Involvement In Nerve Regeneration" *Eur. J. Neurosci.* 5: 1017-1023.

Volonté, C. et al. (1989) "Differential Inhibition of Nerve Growth Factor Responses By Purine Analogues: Correlation With Inhibition Of A Nerve Growth Factor-Activated Protein Kinase" *J. Cell Biol.* 109:2395-2403.

Wakade, T.D. et al. (1995) "Adenosine-induced Apoptosis In Chick Embryonic Sympathetic Neurons: A New Physiological Role For Adenosine" *J. Physiol.* 488(1):123-138.

Zarbin, M.A. et al. (1990) "Anterograde Transport Of Opioid Receptors In Rat Vagus Nerves And Dorsal Roots Of Spinal Nerves: Pharmacology and Sensitivit To Sodium and Guanine Nucleotides" *Exp. Brain Res.* 81:267-278.

Zhou, Tian-Hua et al. (2000) "Identification of a Human Brain-specific Isoform of Mammaliam STE20-like Kinase 3 That Is Regulated by cAMP-dependent Protein Kinase" *J. Biol. Chem.* 275(4):2513-19.

Zurn, A.D. and K.Q. Doe (1988) "Purine Metabolite Inosine Is An Adrenergic Neurotrophic Substance For Cultured Chicken Sympathetic Neurons" *Proc. Natl. Acad. Sci. USA* 85:8301-8305.

* cited by examiner

FIGURE 1

MAHSPVQSGLPGMQNLK...

MST-3b
MDSRAQLWGLALNKRRATLPHPGGSTNLKADPEELFTKLEKIGKGSFGEVFKGIDNRTQK
VVAIKIIDLEEAEDEIEDIQQEITVLSQCDSPYVTKYYGSYLKDTKLWIIMEYLGGGSAL
DLLEPGPLDETQIATILREILKGLDYLHSEKKIHRDIKAANVLLSEHGEVKLADFGVAGQ
LTDTQIKRNTFVGTPFWMAPEVIKQSAYDSKADIWSLGITAIELARGEPPHSELHPMKVL
FLIPKNNPPTLEGNYSKPLKEFVEACLNKEPSFRPTAKELLKHKFILRNAKKTSYLTELI
DRYKRWKAEQSHDDSSSEDSDAETDGQASGGSDSGDWIFTIREKDPKNLENGALQPSDLD
RNKMKDIPKRPFSQCLSTIISPLFAELKEKSQACGGNLGSIEELRGAIYLAEEACPGISD
TMVAQLVQRLQRYSLSGGGTSSH  (443)

FIGURE 2

METHODS AND COMPOSITIONS FOR MODULATING AXONAL OUTGROWTH OF CENTRAL NERVOUS SYSTEM NEURONS

BACKGROUND OF THE INVENTION

Past early childhood, injury to the central nervous system (CNS) results in functional impairments that are largely irreversible. Within the brain or spinal cord, damage resulting from stroke, trauma, or other causes can result in life-long losses in cognitive, sensory and motor functions, and even maintenance of vital functions. Nerve cells that are lost are not replaced, and those that are spared are generally unable to re-grow severed connections, although a limited amount of local synaptic reorganization can occur close to the site of injury. Functions that are lost are currently untreatable.

Regenerative failure in the CNS has been attributed to a number of factors, which include the presence of inhibitory molecules on the surface of glial cells that suppress axonal growth; absence of appropriate substrate molecules such as laminin to foster growth and an absence of the appropriate trophic factors needed to activate programs of gene expression required for cell survival and differentiation.

By contrast, within the peripheral nervous system (PNS), injured nerve fibers can re-grow over long distances, with eventual excellent recovery of function. Within the past 15 years, neuroscientists have come to realize that this is not a consequence of intrinsic differences between the nerve cells of the peripheral and central nervous system; remarkably, neurons of the CNS will extend their axons over great distances if given the opportunity to grow through a grafted segment of PNS (e.g., sciatic nerve). Therefore, neurons of the CNS retain a capacity to grow if given the right signals from the extracellular environment. Factors which contribute to the differing growth potentials of the CNS and PNS include certain growth-inhibiting molecules on the surface of the oligodendrocytes that surround nerve fibers in the CNS, but which are less abundant in the comparable cell population of the PNS (Schwann cells); molecules of the basal lamina and other surfaces that foster growth in the PNS but which are absent in the CNS (e.g., laminin); and trophic factors, soluble polypeptides which activate programs of gene expression that underlie cell survival and differentiation. Although such trophic factors are regarded as essential for maintaining the viability and differentiation of nerve cells, the particular ones that are responsible for inducing axonal regeneration in the CNS remain uncertain.

Moreover, the intracellular molecule(s) that mediates axonal outgrowth of normal neuronal cells (e.g., upon stimulation with extracellular factors or upstream secondary messangers) has not been elucidated. One report has described the partial isolation of a kinase, referred to as "protein kinase N", from rat pheochromocytoma PC12 cells that is activated by NGF treatment of the PC12 cells and sensitive to purine regulation (C. Volonte, et al., (1989) *J. Cell Biol.* 109, 2395–403). However, as PC12 cells are a rat phaeochromocytoma cell line from the adrenal medulla, with many different properties than normal CNS neurons, these cells present a limited model for the processes by which growth of normal CNS neurons is stimulated and the results obtained in PC12 cells may not be predictive of molecules involved in normal CNS neuron growth. Furthermore, this protein kinase N was only partially purified and remains to be molecularly characterized.

In view of the lack of understanding of the molecules involved in mediating axonal outgrowth, effective treatments for CNS injuries have not been developed. Accordingly, elucidation and molecular characterization of such molecules is still necessary, and methods and compositions for modulating the outgrowth of normal CNS neurons by modulating the activity of such molecules are still needed.

SUMMARY OF THE INVENTION

The present invention provides methods and compositions for modulating the axonal outgrowth of central nervous system neurons, in particular normal mammalian central nervous system neurons. The invention is based, at least in part, on the isolation of a highly purified form of the N-kinase polypeptide from normal mammalian neuronal tissue, molecular characterization of its chemical structure (including amino acid sequence), demonstration of its sensitivity to purine regulation and the discovery that this kinase plays an active role in the axonal outgrowth of CNS neurons, including mammalian CNS neurons, such as retinal ganglion neurons. Identification of N-kinase as a critical intracellular mediator of axonal outgrowth, and chemical characterization of its structure, now provides for the ability to modulate axonal outgrowth by modulating N-kinase activity. Furthermore, this purification and characterization of N-kinase now allows for its use in screening assays to identify additional modulators of axonal outgrowth.

Accordingly, in one aspect, the present invention is directed to a method for treating a subject (e.g., a mammal, such as a human) suffering or prone to suffering from a condition characterized by aberrant, e.g., inadequate or insufficient, axonal outgrowth of central nervous system neurons (e.g., stroke, CNS trauma, or a neurodegenerate disease), by administering to the subject a compound that modulates the activity of N-kinase, thereby treating the subject suffering or prone to suffering from a condition characterized by aberrant axonal outgrowth of central nervous system neurons.

The methods of the invention for modulating, e.g., stimulating, the axonal outgrowth of central nervous system neurons can be used following damage or other injury to the CNS neurons (e.g., stroke, Traumatic Brain Injury, cerebral aneurism, spinal cord injury and the like). The methods of the invention for modulating, e.g., inhibiting, the axonal outgrowth of CNS neurons can be used in neuroproliferative disorders where aberrant axonal outgrowth may occur, such as epilepsy (e.g., post-traumatic epilepsy) and neuropathic pain syndrome.

In one aspect, the compound that modulates the activity of N-kinase is administered to a subject in accordance with the present invention by introduction into the central nervous system of the subject, for example into the cerebrospinal fluid of the subject. In certain aspects of the invention, the compound that modulates the activity of N-kinase is introduced intrathecally, for example into a cerebral ventricle, the lumbar area, or the cisterna magna. In a preferred embodiment, the method of the invention modulates outgrowth of damaged cortical neurons. In yet another preferred embodiment, the method of the invention modulates outgrowth of damaged retinal ganglion cells. In such circumstances, the compound that modulates the activity of N-kinase can be administered locally to cortical neurons or retinal ganglion cells to modulate axonal outgrowth.

In yet another aspect of the invention, the compound that modulates the activity of N-kinase is administered in a pharmaceutically acceptable formulation. The pharmaceutically acceptable formulation can be a dispersion system, for example a lipid-based formulation, a liposome formulation, or a multivesicular liposome formulation. The pharmaceutically acceptable formulation can also comprise a polymeric matrix, selected, for example, from synthetic polymers such as polyesters (PLA, PLGA), polyethylene glycol, poloxomers, polyanhydrides, and pluronics or selected from naturally derived polymers, such as albumin, alginate, cellulose derivatives, collagen, fibrin, gelatin, and polysaccharides.

In a preferred embodiment, the pharmaceutically acceptable formulation provides sustained delivery, e.g., "slow release" of the compound that modulates the activity of N-kinase to a subject for at least one week, more preferably at least one month, after the pharmaceutically acceptable formulation is administered to the subject. Preferred approaches for achieving sustained delivery of a formulation of the invention include the use of a slow release polymeric capsules or an infusion pump that includes the formulation.

In one embodiment of the invention, the compound that modulates the activity of N-kinase is a small molecule, the N-kinase polypeptide or fragment thereof, an anti-N-kinase antibody, an antisense N-kinase nucleic acid molecule, a ribozyme, or the N-kinase gene or fragment thereof.

In another aspect, the invention features a method for modulating, e.g., stimulating or inhibiting, axonal outgrowth of a mammalian central nervous system neuron (such as a mammalian central nervous system neuron) by contacting the central nervous system neuron with a compound that modulates the activity of N-kinase, thereby modulating axonal outgrowth of the central nervous system neuron.

In yet another aspect, the invention features a method for modulating the axonal outgrowth of a central nervous system neuron in a subject, by administering to the subject a compound that modulates the activity of N-kinase, such that axonal outgrowth in the subject is modulated.

In a further aspect, the invention features a method for identifying a compound that modulates axonal outgrowth of a central nervous system neuron by contacting N-kinase with a test compound and determining the ability of the test compound to modulate the activity of N-kinase, thereby identifying a compound that modulates axonal outgrowth of a central nervous system neuron. In a preferred embodiment, the ability of the test compound to modulate the activity of N-kinase is determined by assessing the ability of the test compound to modulate N-kinase dependent phosphorylation of a substrate, e.g., a histone HF-1 protein.

In one embodiment, the N-kinase used in the methods of the invention is a human N-kinase, such as a recombinantly produced human N-kinase. In another embodiment, the N-kinase used in the methods of the invention is a bovine N-kinase, such as an N-kinase which is purified from a bovine source, e.g., neonatal bovine brain tissue.

In another embodiment, the screening method of the invention further includes determining the ability of the test compound to modulate axonal outgrowth of a central nervous system neuron.

In another aspect, the invention features a method for identifying a compound that modulates axonal outgrowth of a central nervous system neuron, comprising contacting N-kinase with a test compound, an N-kinase substrate (e.g., a histone HF-1 protein), radioactive ATP (e.g., $[\gamma\text{-}^{32}P]$ ATP), and $Mn^{+2}$; and determining the ability of the test compound to modulate N-kinase dependent phosphorylation of the substrate, thereby identifying a compound that modulates axonal outgrowth of a central nervous system neuron. In a preferred embodiment, the method of the invention further includes determining the ability of the test compound to modulate axonal outgrowth of a central nervous system neuron.

In another aspect, the invention features a compound that modulates axonal outgrowth of a central nervous system neuron identified by any of the foregoing methods.

In yet another aspect, the invention features an isolated N-kinase polypeptide of the type that: (a) is present in neonatal brain tissue (e.g., neonatal human, bovine, rat, or mouse brain tissue); (b) is inhibited by 6-thioguanine; (c) is activated by $Mn^{+2}$ but not by $Mg^{+2}$ or $Ca^{+2}$; (d) has a molecular weight of approximately 49 kDa; and (e) is eluted from a Cibacron Blue column at a NaCl concentration of 1.5–1.75 M.

In a further aspect, the invention features an antibody, e.g., an intracellular antibody, which is specifically reactive with an epitope of the N-kinase polypeptide. In a preferred embodiment, the antibody is reactive with an epitope which includes the ATP binding domain of the N-kinase.

In another aspect, the invention features a fragment of the N-kinase polypeptide, for example, a fragment that includes at least 15, 20, 25, 30, 40, 50, 100, 150, or 200 contiguous amino acids of the N-kinase polypeptide. In a preferred embodiment, the fragment of the N-kinase polypeptide is able to elicit an immune response.

Pharmaceutical compositions, and packaged formulations, comprising a composition of the invention (e.g., compound that modulates the activity of N-kinase) and a pharmaceutically acceptable carrier are also provided by the invention.

Other features and advantages of the invention will be apparent from the following detailed description, and from the claims.

BRIEF DESCRIPTION OF THE DRAWINGS

FIGS. 1A–C are SDS-PAGE gels depicting the purification of the N kinase polypeptide. The N-kinase band at each stage of the purification is indicated by an asterisk. FIG. 1A depicts a prominent 49 kDa band which binds strongly to a Cibacron Blue column and requires 1.5–1.75 M NaCl to be eluted. FIG. 1B depicts the protein fractions obtained from the separation on a C4 hydrophobic-interaction column. Fractions 24–26 contain the N-kinase polypeptide. FIG. 1C depicts the final stage of purification which was accomplished by SDS-PAGE. The band indicated by the asterisk coincided in its migration position with N-kinase activity, as visualized in a parallel gel assayed with the in-gel kinase method.

DETAILED DESCRIPTION

The present invention provides methods and compositions for modulating the axonal outgrowth of central nervous system neurons, in particular mammalian central nervous system neurons. The invention is based, at least in part, on the isolation of a CMZ-129 highly purified form of the N-kinase polypeptide from a mammalian source and the discovery that this kinase plays an active role in the axonal outgrowth of CNS neurons, including mammalian CNS neurons, such as retinal ganglion neurons, or cortical pyramidal cells.

Accordingly, the present invention is directed to a method for treating a subject (e.g., a mammal, such as a human) suffering or prone to suffering from a condition characterized by aberrant axonal outgrowth of central nervous system neurons, (e.g., a condition characterized by a failure of injured central nervous system neurons to regrow their connections) by administering to the subject a compound that modulates the activity of N-kinase, thereby treating the subject suffering or prone to suffering from a condition characterized by aberrant axonal outgrowth of central nervous system neurons.

The methods of the invention for modulating, e.g., stimulating, the axonal outgrowth of central nervous system neurons can be used following damage or other injury to the CNS neurons (e.g., stroke, Traumatic Brain Injury, cerebral aneurism, spinal cord injury and the like). The methods of the invention for modulating, e.g., inhibiting, the axonal outgrowth of CNS neurons can be used in neuroproliferative disorders where aberrant axonal outgrowth may occur, such as epilepsy (e.g., post-traumatic epilepsy) and neuropathic pain syndrome.

Figure 2:
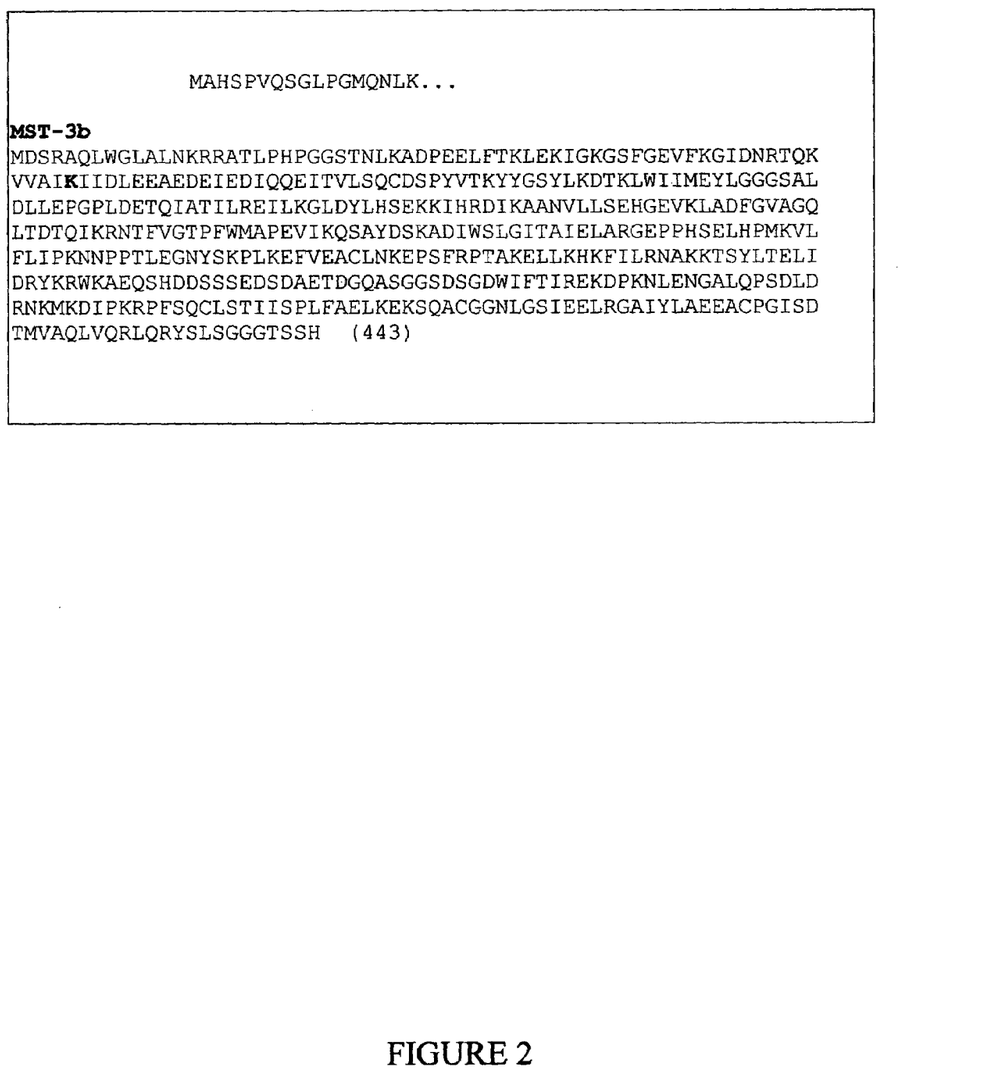
FIG. 2 depicts the amino acid (SEQ ID NO: 1) sequence of the human N-kinase. Direct matches between the purified protein and the published sequence are shown in blue. K65 (bold type) lies in the ATP-binding region of the kinase domain.

As used herein, the term "N-kinase" includes all forms of N-kinase including but not limited to human N-kinase, bovine N-kinase, murine N-kinase, rat N-kinase, and porcine N-kinase. The amino acid and nucleotide sequences of the human N-kinase are described in Zhou T-H. et al. (2000) *J. Biol. Chem.* 275(4):2513–2519 and in GenBank Accession Number AF083420, the contents of which are incorporated herein by reference. The amino acid sequence of the human N-kinase is shown in FIG. 2 and in SEQ ID NO: 1. In a preferred embodiment, the term "N-kinase" includes the isoform of N-kinase that is inhibited by 6-thioguanine, that is activated by $Mn^{+2}$ but not by $Mg^{+2}$ or $Ca^{+2}$, and that has a molecular weight of approximately 49 kDa.

As used herein, the language "a compound that modulates the activity of N-kinase" includes any compound which has the ability to modulate, e.g., stimulate or inhibit, the activity of N-kinase as determined by, for example, the assays described herein. Such compounds are able to modulate one or more of the following: (a) the ability of N-kinase to phosphorylate a substrate, e.g., a histone HF-1 protein; (b) the ability of N-kinase to interact with, e.g., bind to, a non-N-kinase molecule, such as a downstream molecule in the axonal outgrowth signaling pathway; (c) the ability of N-kinase to bind ATP or $Mn^{+2}$; or (d) the ability of N-kinase to modulate the axonal outgrowth of central nervous system neurons.

In a preferred embodiment, the compound that modulates the activity of N-kinase acts downstream of AF-1 or other growth factors in the axonal outgrowth signaling pathway. The ability of the compound to act downstream of AF-1 or other growth factors in the axonal outgrowth signaling pathway may be determined using one of the assays described herein. For example, once a compound has been determined to be capable of stimulating the activity of N-kinase (e.g., stimulating the N-kinase dependent phosphorylation of a substrate), N-kinase may be contacted both with this compound and with 6-thioguanine. The inability of 6-thioguanine to inhibit the stimulatory effect of the compound would indicate that the compound is acting downstream of 6-thioguanine in the axonal outgrowth signaling pathway, whereas the ability of 6-thioguanine to inhibit the stimulatory effect of the compound would indicate that the compound is acting upstream (or at the same point) in the signaling pathway.

Alternatively, once a compound has been determined to be capable of inhibiting the activity of N-kinase (e.g., inhibiting the N-kinase dependent phosphorylation of a substrate), N-kinase may be contacted both with this compound and with inosine. The inability of inosine to counteract the inhibitory effect of the compound would indicate that the compound is acting downstream of inosine in the axonal outgrowth signaling pathway, whereas the ability of inosine to counteract the inhibitory effect of the compound would indicate that the compound is acting upstream (or at the same point) in the signaling pathway.

In certain embodiments of the invention, the compound that modulates the activity of N-kinase can be any compound with the proviso that it is not a purine base (e.g., guanine, inosine, adenosine, and xanthine), such as a purine base linked to sugars, such as ribose, deoxyribose, and analogs and derivatives thereof. In certain other embodiments of the invention, the compound that modulates the activity of N-kinase can be any compound with the proviso that it is not a purine base analog or derivative thereof.

Examples of compounds that modulate the activity of N-kinase include small molecules, the N-kinase polypeptide or fragments thereof, an anti-N-kinase antibody, an antisense N-kinase nucleic acid molecule, a ribozyme, or the N-kinase gene or fragments thereof.

As used herein, the term "small molecule" includes, but is not limited to, peptides, peptidomimetics, amino acids, amino acid analogs, polynucleotides, polynucleotide analogs, nucleotides, nucleotide analogs, organic or inorganic compounds (i.e.,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

As used herein, the language "modulating the axonal outgrowth of central nervous system neurons" is intended to include the capacity to stimulate or inhibit axonal outgrowth of central nervous system neurons to various levels, e.g., to levels which allow for the treatment of a targeted CNS condition.

As used herein, the term "outgrowth" (i.e., axonal outgrowth) refers to the process by which axons grow out of a CNS neuron. The outgrowth can result in a totally new axon or the repair of a partially damaged axon. Outgrowth is typically evidenced by extension of an axonal process of at least 5 cell diameters in length. Moreover, axonal outgrowth can be evidenced by GAP-43 expression (which can be detected by, for example, immunostaining).

As used herein, the term "CNS neurons" is intended to include the neurons of the brain and the spinal cord which are unresponsive to nerve growth factor (NGF). The term is not intended to include support or protection cells such as astrocytes, oligodentrocytes, microglia, ependyma and the like, nor is it intended to include peripheral nervous system (e.g., somatic, autonomic, sympathetic or parasympathetic nervous system) neurons. Preferred CNS neurons are mammalian neurons, more preferably human neurons.

As used herein, the language "contacting" is intended to include both in vivo or in vitro methods of bringing a compound that modulates the activity of N-kinase into proximity with a CNS neuron, such that the compound that modulates the activity of N-kinase can modulate the outgrowth of axonal processes from the CNS neuron.

As used herein, the term "subject" is intended to include animals susceptible to conditions characterized by aberrant, e.g., insufficient, axonal outgrowth of central nervous system neurons, preferably mammals, most preferably humans. In a preferred embodiment, the subject is a primate. In an even more preferred embodiment, the primate is a human. Other examples of subjects include dogs, cats, goats, and cows.

As used herein, the term "condition characterized by aberrant axonal outgrowth of central nervous system neurons" is intended to include a disease, disorder, or condition which is caused or characterized by an aberrant, e.g., increased, insufficient, inadequate, or decreased, axonal outgrowth of central nervous system neurons. Such conditions directly or indirectly affect the normal functioning of the central nervous system (CNS). A condition characterized by aberrant, e.g., insufficient, axonal outgrowth of central nervous system neurons includes, but is not limited to, an injury to the optic nerve, e.g., affecting retinal ganglion cells; traumatic brain injury; stroke; cerebral aneurism; spinal cord injury, including monoplegia, diplegia, paraplegia, hemiplegia and quadriplegia; neuroproliferative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, Jakob-Creutzfieldt disease, or AIDS related dementias; epilepsy, e.g., posttraumatic brain injury; or neuropathic pain syndrome.

As used herein, the term "stroke" is art recognized and is intended to include sudden diminution or loss of consciousness, sensation, and voluntary motion caused by rapture or obstruction (e.g., by a blood clot) of an artery of the brain.

As used herein, the term "Traumatic Brain Injury" is art recognized and is intended to include the condition in which, a traumatic blow to the head causes damage to the brain or connecting spinal cord, often without penetrating the skull. Usually, the initial trauma can result in expanding hematoma, subarachnoid hemorrhage, cerebral edema, raised intracranial pressure (ICP), and cerebral hypoxia, which can, in turn, lead to severe secondary events due to low cerebral blood flow (CBF).

In another aspect, the invention features a method for modulating, e.g., stimulating or inhibiting, axonal outgrowth of a central nervous system neuron (such as a mammalian central nervous system neuron) by contacting the central nervous system neuron with a compound that modulates the activity of N-kinase, thereby modulating axonal outgrowth of the central nervous system neuron.

In yet another aspect, the invention features a method for modulating the axonal outgrowth of a central nervous system neuron in a subject, by administering to the subject a compound that modulates the activity of N-kinase, such that axonal outgrowth in the subject is modulated.

In yet another aspect, the invention features an isolated N-kinase polypeptide of the type that: (a) is present in neonatal brain tissue (e.g., neonatal human, bovine, rat, or mouse brain tissue); (b) is inhibited by 6-thioguanine; (c) is activated by $Mn^{+2}$ but not by $Mg^{+2}$ or $Ca^{+2}$; (d) has a molecular weight of approximately 49 kDa; and (e) is eluted from a Cibacron Blue column at a NaCl concentration of 1.5–1.75 M. As used herein, an "isolated" N-kinase polypeptide is substantially free (i.e., greater than 95% free) of cellular material or other contaminating proteins from the cell or tissue source from which the N-kinase protein is derived, or substantially free from chemical precursors or other chemicals when chemically synthesized. The language "substantially free of cellular material" includes preparations of N-kinase in which the protein is separated from cellular components of the cells from which it is isolated or recombinantly produced. In one embodiment, the language "substantially free of cellular material" includes preparations of N-kinase protein having less than about 20% (by dry weight) of non-N-kinase protein (i.e., contaminating protein), more preferably less than about 10% of non-N-kinase protein, still more preferably less than about 5% of non-N-kinase protein, and most preferably less than about 3% non-N-kinase protein. When the N-kinase protein or biologically active portion thereof is recombinantly produced, it is also preferably substantially free of culture medium, i.e., culture medium represents less than about 20%, more preferably less than about 10%, and most preferably less than about 5% of the volume of the protein preparation.

Various aspects of the invention are described in further detail in the following subsections:

Method for Identifying a Compound that Modulates Axonal Outgrowth of a Central Nervous System Neuron In one aspect, the invention features a method for identifying a compound that modulates axonal outgrowth of a central nervous system neuron by contacting N-kinase with a test compound and determining the ability of the test compound to modulate the activity of N-kinase, thereby identifying a compound that modulates axonal outgrowth of a central nervous system neuron.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al (1992) *Proc Natl. Acad. Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses an N-kinase protein or biologically active portion thereof is contacted with a test compound and the ability of the test compound to modulate N-kinase activity is determined. Determining the ability of the test compound to modulate N-kinase activity can be accomplished by monitoring, for example, the production of one or more specific metabolites in a cell which expresses N-kinase (see, e.g., Saada et al. (2000) *Biochem Biophys. Res. Commun.* 269: 382–386). The cell, for example, can be of mammalian origin, e.g., a neuronal cell.

Determining the ability of the test compound to modulate N-kinase activity can further be accomplished by, for example, determining the ability of N-kinase to phosphorylate a substrate. The ability of N-kinase to phosphorylate a substrate (e.g., a histone HF-1 protein) can be determined by, for example, an in vitro kinase assay. Briefly, the N-kinase can be incubated with the substrate and radioactive ATP, e.g., [γ-$^{32}$P] ATP, in a buffer containing $MnCl_2$, e.g., 5 mM $MnCl_2$. Following the incubation, the substrate can be immunoprecipitated or precipitated with TCA or collected on a filter (if no other kinases are present) and separated by SDS-polyacrylamide gel electrophoresis under reducing conditions, transferred to a membrane, e.g., a PVDF membrane, and autoradiographed. The appearance of detectable bands on the autoradiograph indicates that the substrate has been phosphorylated. Alternatively, the in-gel assays described in Example 1 may be used to determine the ability of N-kinase to phosphorylate a substrate. Phosphoaminoacid analysis of the phosphorylated substrate can also be performed in order to determine which residues on the protein are phosphorylated. Briefly, the radiophosphorylated protein band can be excised from the SDS gel and subjected to partial acid hydrolysis. The products can then be separated by one-dimensional electrophoresis and analyzed on, for example, a phosphoimager and compared to ninhydrin-stained phosphoaminoacid standards.

The ability of the test compound to modulate N-kinase binding to a non-N-kinase molecule, such as a downstream molecule in the axonal outgrowth signaling pathway, can also be determined. Determining the ability of the test compound to modulate N-kinase binding to a non-N-kinase molecule can be accomplished, for example, by coupling the non-N-kinase molecule with a radioisotope or enzymatic label such that binding of the non-N-kinase molecule to N-kinase can be determined by detecting the labeled non-N-kinase molecule in a complex.

It is also within the scope of this invention to determine the ability of a test compound to interact with, e.g., bind to, N-kinase or biologically active portions thereof. Preferred biologically active portions of the N-kinase proteins to be used in assays of the present invention include fragments which participate in interactions with non-N-kinase molecules, e.g., fragments with high surface probability scores. Determining the ability of the test compound to bind N-kinase can be accomplished, for example, by coupling the compound with a radioisotope or enzymatic label such that binding of the compound to N-kinase can be determined by detecting the labeled N-kinase compound in a complex. For example, test compounds can be labeled with $^{125}$I, $^{35}$S, $^{14}$C, or $^3$H, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

Determining the ability of a test compound to interact with N-kinase may also be accomplished without the labeling of any of the interactants. For example, a microphysiometer can be used to detect the interaction of a compound with N-kinase without the labeling of either the compound or the N-kinase. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and N-kinase.

Determining the ability of the test compound to bind to N-kinase or a biologically active portion thereof, can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of N-kinase can be accomplished by determining the ability of the N-kinase protein to further modulate the activity of a downstream effector of an N-kinase target molecule. For example, the activity of the effector molecule on an appropriate target can be determined or the binding of the effector to an appropriate target can be determined as previously described.

In more than one embodiment of the above assay methods of the present invention, it may be desirable to immobilize any of the reactants, e.g., N-kinase or a non-N-kinase molecule, to facilitate separation of complexed from uncomplexed forms of one or both of the proteins, as well as to accommodate automation of the assay. Binding of a test compound to N-kinase, or interaction of N-kinase with a non-N-kinase molecule in the presence and absence of a test compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/N-kinase fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed non-N-kinase molecule or N-kinase, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of N-kinase binding or activity determined using standard techniques.

Other techniques for immobilizing proteins on matrices can also be used in the screening assays of the invention. For example, either N-kinase or a non-N-kinase molecule can be immobilized utilizing conjugation of biotin and streptavidin. Biotinylated N-kinase or non-N-kinase molecule can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with N-kinase or a non-N-kinase molecule but which do not interfere with the binding of N-kinase to its target non-N-kinase molecule can be derivatized to the wells of the plate, and unbound non-N-kinase molecule or N-kinase trapped in the wells by antibody conjugation. Methods for detecting such complexes, in addition to those described above for the GST-immobilized complexes, include immunodetection of complexes using antibodies reactive with N-kinase or a non-N-kinase molecule, as well as enzyme-linked assays which rely on detecting an enzymatic activity associated with N-kinase or a non-N-kinase target molecule.

In another embodiment, modulators of N-kinase expression are identified in a method wherein a cell is contacted with a candidate compound and the expression of N-kinase mRNA or protein in the cell is determined. The level of expression of N-kinase mRNA or protein in the presence of the candidate compound is compared to the level of expression of N-kinase mRNA or protein in the absence of the candidate compound. The candidate compound can then be identified as a modulator of N-kinase expression based on this comparison. For example, when expression of N-kinase mRNA or protein is greater (statistically significantly greater) in the presence of the candidate compound than in its absence, the candidate compound is identified as a stimulator of N-kinase mRNA or protein expression. Alternatively, when expression of N-kinase mRNA or protein is less (statistically significantly less) in the presence of the candidate compound than in its absence, the candidate compound is identified as an inhibitor of N-kinase mRNA or protein expression. The level of N-kinase mRNA or protein expression in the cells can be determined by methods described herein for detecting N-kinase mRNA or protein.

In yet another aspect of the invention, the N-kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with N-kinase ("N-kinase-binding proteins" or "N-kinase-bp") and are involved in N-kinase activity. Such N-kinase-binding proteins are also likely to be involved in the propagation of signals by the N-kinase proteins or N-kinase targets as, for example, downstream elements of an N-kinase-mediated signaling pathway. Alternatively, such N-kinase-binding proteins are likely to be N-kinase inhibitors.

The two-hybrid system is based on the modular nature of most transcription factors, which consist of separable DNA-binding and activation domains. Briefly, the assay utilizes two different DNA constructs. In one construct, the gene that codes for an N-kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an N-kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the N-kinase protein.

In another aspect, the invention pertains to a combination of two or more of the assays described herein. For example, a modulating compound can be identified using a cell-based or a cell free assay, and the ability of the compound to modulate the activity of an N-kinase protein can be confirmed in vivo, e.g., in an animal such as an animal model for a condition characterized by aberrant, e.g., insufficient axonal outgrowth of central nervous system neurons. Examples of such animal models are described in, for example, Benowitz et al. (1999) *PNAS* 96(23): 13486–90. Epilepsy animal models are also known in the art.

This invention further pertains to novel compounds identified by the above-described screening assays. Accordingly, it is within the scope of this invention to further use a compound identified as described herein in an appropriate animal model. For example, a compound identified as described herein (e.g., an N-kinase modulating compound, an antisense N-kinase nucleic acid molecule, an N-kinase-specific antibody, or an N-kinase-binding partner) can be used in an animal model to determine the efficacy, toxicity, or side effects of treatment with such a compound. Alternatively, a compound identified as described herein can be used in an animal model to determine the mechanism of action of such a compound. Furthermore, this invention pertains to uses of novel compounds identified by the above-described screening assays for treatments as described herein.

In one embodiment, the N-kinase used in the methods of the invention is a human N-kinase, such as a recombinantly produced N-kinase. N-kinase, e.g., human N-kinase, may be introduced into a recombinant expression vector using standard techniques and expressed in prokaryotic or eukaryotic cells. For example, N-kinase, e.g., human N-kinase, can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, a recombinant expression vector containing N-kinase, e.g., human N-kinase, can be transcribed and translated in vitro, for example using T7 promoter regulatory sequences and T7 polymerase.

In another embodiment, the N-kinase used in the methods of the invention is a bovine N-kinase, such as an N-kinase which is purified from a bovine source, e.g., neonatal bovine brain tissue, as described herein in, for instance, Example 1.

In another embodiment, the method of the invention further includes determining the ability of the test compound to modulate axonal outgrowth of a central nervous system neuron. Determining the ability of the test compound to modulate axonal outgrowth of a central nervous system neuron can be accomplished by, for example, using dissociated cultures of purified rat retinal ganglion cells. Dissociated cultures of purified rat retinal ganglion cells can, for example, be prepared by immunopanning as described in Barres et al, Neuron, 1: 791–803,1988, the contents of which are incorporated herein by reference. In brief, retinas from Sparague-Dawley rats can be dissociated using papain activated with cysteine. Macrophages are removed by incubation with an anti-rat macrophage antibody (Accurate) followed by immunopanning with an anti-rabbit IgG antibody. Ganglion cells are isolated by immunopanning with an anti-Thy-1 antibody, then dislodged with trypsin for use in low-density cultures. Rat retinal ganglion cells are maintained at 37° C. in a $CO_2$ incubator using the same medium described above except for the presence of 30 mM bicarbonate.

Samples are plated in quadruplicate in randomized positions of a 24-well plate, contacted with the test compound, and the code is concealed to ensure that growth is evaluated in a blinded fashion. Each experiment may contain 4 wells of a negative control (media plus supplements only) and 4 wells of a positive control (e.g., a standardized AF-1 sample of known activity). Growth and survival are assessed after 6 days for all ganglion cells in 25 consecutive fields of each well using phase contrast microscopy at 400× magnification (c. 150 ganglion cells counted per well). Extension of a process 5 cell diameters in length is used as the criterion for growth, since it clearly distinguishes stimulated cells from negative controls (Schwalb et al., 1995). After the completion of counting, the code is broken, the data tabulated, and means and standard errors are calculated for the 4 replicate wells of each sample using Cricket Graph (CA Associates, Islandia, N.Y.). Data are normalized by subtracting the growth in the negative controls (usually 4–5%) and dividing by the net growth in the positive controls.

Goldfish retinal ganglion cells (Benowitz et al. (1998) *J. Biol. Chem.* 273(45):29626–34) as well as mixtures of rat and goldfish ganglion cells may also be used.

Compounds that Modulate Axonal Outgrowth of a Central Nervous System Neuron

In another aspect, the invention features a compound that modulates axonal outgrowth of a central nervous system neuron identified by any of the foregoing methods.

In one embodiment, the compound that modulates axonal outgrowth of a central nervous system neuron is an antisense N-kinase nucleic acid molecule. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to the entire N-kinase coding strand, or to only a portion thereof. In one embodiment, an antisense nucleic acid molecule is antisense to a "coding region" of the coding strand of a nucleotide sequence encoding an N-kinase. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding N-kinase. The term "noncoding region" refers to 5' and 3' sequences which flank the coding region that are not translated into amino acids (i.e., also referred to as 5' and 3' untranslated regions).

Given the coding strand sequence encoding N-kinase, antisense nucleic acids of the invention can be designed according to the rules of Watson and Crick base pairing. The antisense nucleic acid molecule can be complementary to the entire coding region of N-kinase mRNA, but more preferably is an oligonucleotide which is antisense to only a portion of the coding or noncoding region of N-kinase mRNA. For example, the antisense oligonucleotide can be complementary to the region surrounding the translation start site of N-kinase mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an N-kinase protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site, e.g., in the brain. Alternatively, antisense nucleic acid molecules can be modified to target selected cells and then administered systemically.

For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense N-kinase nucleic acid molecule may be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-O—methylribonucleotide (Inoue et al. (1987) *Nucleic Acids Res.* 15:6131–6148) or a chimeric RNA-DNA analogue (Inoue et al. (1987) FEBS Lett. 215: 327–330).

In still another embodiment, the compound that modulates axonal outgrowth of a central nervous system neuron is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave N-kinase mRNA transcripts to thereby inhibit translation of N-kinase mRNA. A ribozyme having specificity for an N-kinase-encoding nucleic acid can be designed based upon the nucleotide sequence of an N-kinase cDNA. For example, a derivative of a Tetrahymena L-19 IVS RNA can be constructed in which the nucleotide sequence of the active site is complementary to the nucleotide sequence to be cleaved in an N-kinase-encoding mRNA. See, e.g., Cech et al. U.S. Pat. No. 4,987,071; and Cech et al. U.S. Pat. No. 5,116,742. Alternatively, N-kinase mRNA can be used to select a catalytic RNA having a specific ribonuclease activity from a pool of RNA molecules. See, e.g., Bartel, D. and Szostak, J. W. (1993) Science 261:1411–1418.

Alternatively, N-kinase gene expression can be inhibited by targeting nucleotide sequences complementary to the regulatory region of the N-kinase (e.g., the N-kinase promoter and/or enhancers) to form triple helical structures that prevent transcription of the N-kinase gene in target cells. See generally, Helene, C. (1991) *Anticancer Drug Des.* 6(6): 569–84; Helene, C. et al. (1992) *Ann. N.Y. Acad. Sci.* 660:27–36; and Maher, L. J. (1992) *Bioassays* 14(12): 807–15.

In still another embodiment, the compound that modulates axonal outgrowth of a central nervous system neuron is an anti-N-kinase antibody. A full-length N-kinase protein or, alternatively, antigenic peptide fragments of N-kinase may be used as immunogens to generate anti-N-kinase antibodies. The antigenic peptide of N-kinase comprises at least 8 amino acid residues of the amino acid sequence shown in SEQ ID NO:1 and encompasses an epitope of N-kinase such that an antibody raised against the peptide forms a specific immune complex with the N-kinase protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of N-kinase that are located on the surface of the protein, e.g., hydrophilic regions, as well as regions with high antigenicity.

An N-kinase immunogen typically is used to prepare antibodies by immunizing a suitable subject, (e.g., rabbit, goat, mouse or other mammal) with the immunogen. An appropriate immunogenic preparation can contain, for example, recombinantly expressed N-kinase protein or a chemically synthesized N-kinase polypeptide. The preparation can further include an adjuvant, such as Freund's complete or incomplete adjuvant, or similar immunostimulatory agent. Immunization of a suitable subject with an immunogenic N-kinase preparation induces a polyclonal anti-N-kinase antibody response.

The term "antibody" as used herein includes immunoglobulin molecules and immunologically active portions of immunoglobulin molecules, i.e., molecules that contain an antigen binding site which specifically binds (immunoreacts with) an antigen, such as an N-kinase. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind N-kinase molecules. The term "monoclonal antibody" or "monoclonal antibody composition", as used herein, refers to a population of antibody molecules that contain only one species of an antigen binding site capable of immunoreacting with a particular epitope of N-kinase. A monoclonal antibody composition thus typically displays a single binding affinity for a particular N-kinase protein with which it immunoreacts.

Polyclonal anti-N-kinase antibodies can be prepared as described above by immunizing a suitable subject with an N-kinase immunogen. The anti-N-kinase antibody titer in the immunized subject can be monitored over time by standard techniques, such as with an enzyme linked immunosorbent assay (ELISA) using immobilized N-kinase. If desired, the antibody molecules directed against N-kinase can be isolated from the mammal (e.g., from the blood) and further purified by well known techniques, such as protein A chromatography to obtain the IgG fraction. At an appropriate time after immunization, e.g., when the anti-N-kinase antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem* 0.255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with an N-kinase immunogen as described above, and the culture supernatants of the resulting hybridoma cells are screened to identify a hybridoma producing a monoclonal antibody that binds N-kinase.

Any of the many well known protocols used for fusing lymphocytes and immortalized cell lines can be applied for the purpose of generating an anti-N-kinase monoclonal antibody (see, e.g., G. Galfre et al. (1977) *Nature* 266: 55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag-4-1, P3-x63-Ag8.653 or Sp2/O–Ag14 myeloma lines. These myeloma lines are available from ATCC Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind N-kinase, e.g., using a standard ELISA assay.

Alternative to preparing monoclonal antibody-secreting hybridomas, a monoclonal anti-N-kinase antibody can be identified and isolated by screening a recombinant combinatorial immunoglobulin library (e.g., an antibody phage display library) with N-kinase to thereby isolate immunoglobulin library members that bind N-kinase. Kits for generating and screening phage display libraries are commercially available (e.g., the Pharmacia *Recombinant Phage Antibody System*, Catalog No. 27–9400–01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) Bio/Technology 9:1370–1372; Hay et al. (1992) *Hum. Antibod Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-N-kinase antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) Science 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

In one embodiment, the compound that modulates axonal outgrowth of a central nervous system neuron is an intracellular antibody specific for N-kinase. The use of intracellular antibodies to inhibit protein function in a cell is known in the art (see e.g., Carlson, J. R. (1988) *Mol. Cell. Biol.* 8:2638–2646; Biocca, S. et al. (1990) *EMBO J.* 9:101–108; Werge, T. M. et al. (1990) *FEBS Letters* 274:193–198; Carlson, J. R. (1993) *Proc. Natl. Acad. Sci. USA* 90:7427–7428; Marasco, W. A. et al. (1993) *Proc. Natl. Acad. Sci. USA* 90:7889–7893; Biocca, S. et al. (1994) *Bio/Technology* 12:396–399; Chen, S-Y. et al. (1994) *Human Gene Therapy* 5:595–601; Duan, L et al. (1994) *Proc. Natl. Acad. Sci. USA* 91:5075–5079; Chen, S-Y. et al. (1994) *Proc. Natl. Acad. Sci. USA* 91:5932–5936; Beerli, R. R. et al. (1994) *J. Biol. Chem.* 269:23931–23936; Beerli, R. R. et al. (1994) *Biochem. Biophys. Res. Commun.* 204: 666–672; Mhashilkar, A. M. et al. (1995) *EMBO J.* 14:1542–1551; Richardson, J. H. et al. (1995) *Proc. Natl. Acad. Sci. USA* 92:3137–3141; PCT Publication No. WO 94/02610 by Marasco et al.; and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell.

In still another embodiment, the compound that modulates axonal outgrowth of a central nervous system neuron is a small molecule. As used herein, the term "small molecule" includes, but is not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In still another embodiment, the compound that modulates axonal outgrowth of a central nervous system neuron is an N-kinase polypeptide or portion thereof, e.g., a fragment that includes at least 15, 20, 25, 30, 40, 50, 60, 70, 80, 90, 100, 150, or 200 contiguous amino acids of the N-kinase polypeptide. For example, the compound could comprise the constitutively active catalytic domain of the N-kinase.

In still another embodiment, the compound that modulates axonal outgrowth of a central nervous system neuron is an N-kinase gene or portion thereof.

Pharmaceutically Acceptable Formulations

Pharmaceutical compositions, and packaged formulations, comprising a composition of the invention (e.g., compound that modulates the activity of N-kinase) and a pharmaceutically acceptable carrier are also provided by the invention. In the method of the invention, the compound that modulates the activity of N-kinase can be administered in a pharmaceutically acceptable formulation. Such pharmaceutically acceptable formulation typically includes the compound that modulates the activity of N-kinase as well as a pharmaceutically acceptable carrier(s) and/or excipient(s). As used herein, "pharmaceutically acceptable carrier" includes any and all solvents, dispersion media, coatings, antibacterial and anti fungal agents, isotonic and absorption delaying agents, and the like that are physiologically compatible. For example, the carrier can be suitable for injection into the cerebrospinal fluid. Excipients include pharmaceutically acceptable stabilizers and disintegrants. The present invention pertains to any pharmaceutically acceptable formulations, including synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes.

In one embodiment, the pharmaceutically acceptable formulations comprise a polymeric matrix. The terms "polymer" or "polymeric" are art-recognized and include a structural framework comprised of repeating monomer units which is capable of delivering a compound that modulates the activity of N-kinase such that treatment of a targeted condition, e.g., a CNS injury, occurs. The terms also include co-polymers and homopolymers e.g., synthetic or naturally occurring. Linear polymers, branched polymers, and cross-linked polymers are also meant to be included.

For example, polymeric materials suitable for forming the pharmaceutically acceptable formulation employed in the present invention, include naturally derived polymers such as albumin, alginate, cellulose derivatives, collagen, fibrin, gelatin, and polysaccharides, as well as synthetic polymers such as polyesters (PLA, PLGA), polyethylene glycol, poloxomers, polyanhydrides, and pluronics. These polymers are biocompatible with the nervous system, including the central nervous system, they are biodegradable within the central nervous system without producing any toxic byproducts of degradation, and they possess the ability to modify the manner and duration of compound that modulates the activity of N-kinase release by manipulating the polymer's kinetic characteristics. As used herein, the term "biodegradable" means that the polymer will degrade over time by the action of enzymes, by hydrolytic action and/or by other similar mechanisms in the body of the subject. As used herein, the term "biocompatible" means that the polymer is compatible with a living tissue or a living organism by not being toxic or injurious and by not causing an immunological rejection.

Polymers can be prepared using methods known in the art (Sandler, S. R.; Karo, W. *Polymer Syntheses*; Harcourt Brace: Boston, 1994; Shalaby, W.; Ikada, Y.; Langer, R.; Williams, J. *Polymers of Biological and Biomedical Significance* (*ACS Symposium Series* 540; American Chemical Society: Washington, D.C., 1994). Polymers can be designed to be flexible; the distance between the bioactive side-chains and the length of a linker between the polymer backbone and the group can be controlled. Other suitable polymers and methods for their preparation are described in U.S. Pat. Nos. 5,455,044 and 5,576,018, the contents of which are incorporated herein by reference.

The polymeric formulations can be formed by dispersion of the compound that modulates the activity of N-kinase within liquefied polymer, as described in U.S. Pat. No. 4,883,666, the teachings of which are incorporated herein by reference or by such methods as bulk polymerization, interfacial polymerization, solution polymerization and ring polymerization as described in Odian G., Principles of Polymerization and ring opening polymerization, 2nd ed., John Wiley & Sons, New York, 1981, the contents of which are incorporated herein by reference. The properties and characteristics of the formulations are controlled by varying such parameters as the reaction temperature, concentrations of polymer and compound that modulates the activity of N-kinase, types of solvent used, and reaction times.

The compound that modulates the activity of N-kinase can be encapsulated in one or more pharmaceutically acceptable polymers, to form a microcapsule, microsphere, or microparticle, terms used herein interchangeably. Microcapsules, microspheres, and microparticles are conventionally free-flowing powders consisting of spherical particles of 2 millimeters or less in diameter, usually 500 microns or less in diameter. Particles less than 1 micron are conventionally referred to as nanocapsules, nanoparticles or nanospheres. For the most part, the difference between a microcapsule and a nanocapsule, a microsphere and a nanosphere, or microparticle and nanoparticle is size; generally there is little, if any, difference between the internal structure of the two. In one aspect of the present invention, the mean average diameter is less than about 45 μm, preferably less than 20 μm, and more preferably between about 0.1 and 10 μm.

In another embodiment, the pharmaceutically acceptable formulations comprise lipid-based formulations. Any of the known lipid-based drug delivery systems can be used in the practice of the invention. For instance, multivesicular liposomes (MVL), multilamellar liposomes (also known as multilamellar vesicles or "MLV"), unilamellar liposomes, including small unilamellar liposomes (also known as unilamellar vesicles or "SUV") and large unilamellar liposomes (also known as large unilamellar vesicles or "LUV"), can all be used so long as a sustained release rate of the encapsulated compound that modulates the activity of N-kinase or analogue thereof can be established. In one embodiment, the lipid-based formulation can be a multivesicular liposome system. Methods of making controlled release multivesicular liposome drug delivery systems is described in PCT Application Serial Nos. US96/11642, US94/12957 and US94/04490, the contents of which are incorporated herein by reference.

The composition of the synthetic membrane vesicle is usually a combination of phospholipids, usually in combination with steroids, especially cholesterol. Other phospholipids or other lipids may also be used.

Examples of lipids useful in synthetic membrane vesicle production include phosphatidylglycerols, phosphatidylcholines, phosphatidylserines, phosphatidylethanolamines, sphingolipids, cerebrosides, and gangliosides. Preferably phospholipids including egg phosphatidylcholine, dipalmitoylphosphatidylcholine, distearoylphosphatidylcholine, dioleoylphosphatidylcholine, dipalmitoylphosphatidylglycerol, and dioleoylphosphatidylglycerol are used.

In preparing lipid-based vesicles containing a compound that modulates the activity of N-kinase or analogue thereof, such variables as the efficiency of compound that modulates the activity of N-kinase encapsulation, lability of the compound that modulates the activity of N-kinase, homogeneity and size of the resulting population of vesicles, compound that modulates the activity of N-kinase-to-lipid ratio, permeability, instability of the preparation, and pharmaceutical acceptability of the formulation should be considered (see Szoka, et al., *Annual Reviews of Biophysics and Bioengineering*, 9:467, 1980; Deamer, et al., in *Liposomes*, Marcel Dekker, New York, 1983, 27; and Hope, et al., *Chem. Phys. Lipids*, 40:89, 1986, the contents of which are incorporated herein by reference).

Administration of the Pharmaceutically Acceptable Formulation

The pharmaceutically acceptable formulations of the invention are administered such that the compound that modulates the activity of N-kinase, or analogue thereof, comes into contact with central nervous system neurons to thereby modulate the axonal outgrowth thereof. Both local and systemic administration of the formulations are contemplated by the invention, although local administration may be preferable to achieve effective local concentrations of the compound that modulates the activity of N-kinase, or analogue, as well as to avoid possible side effects from systemic administration of the agent. In one embodiment, the compound that modulates the activity of N-kinase is administered by introduction into the central nervous system of the subject, e.g., into the cerebrospinal fluid of the subject. In certain aspects of the invention, the compound that modulates the activity of N-kinase is introduced intrathecally, e.g., into a cerebral ventricle, the lumbar area, or the cisterna magna. In another aspect, the compound that modulates the activity of N-kinase is introduced intraocularly, to thereby contact retinal ganglion cells.

The pharmaceutically acceptable formulations can easily be suspended in aqueous vehicles and introduced through conventional hypodermic needles or using infusion pumps. Prior to introduction, the formulations can be sterilized with, preferably, gamma radiation or electron beam sterilization, described in U.S. Pat. No. 436,742 the contents of which are incorporated herein by reference.

In one embodiment, the compound that modulates the activity of N-kinase formulation described herein is administered to the subject in the period from the time of, for example, an injury to the CNS up to about 100 or 200 hours after the injury has occurred, for example, within 48, 36, 24, 12, or 6 hours from the time of injury. In another embodiment, the compound that modulates the activity of N-kinase is administered to a subject suffering from a chronic injury to the CNS. Accordingly, the compound is administered to the subject over the subject's life time.

In another embodiment of the invention, the compound that modulates the activity of N-kinase formulation is administered into a subject intrathecally. As used herein, the term "intrathecal administration" is intended to include delivering a compound that modulates the activity of N-kinase formulation directly into the cerebrospinal fluid of a subject, by techniques including lateral cerebroventricular injection through a burrhole or cisternal or lumbar puncture or the like (described in Lazorthes et al. Advances in Drug Delivery Systems and Applications in Neurosurgery, 143–192 and Omaya et al., Cancer Drug Delivery, 1: 169–179, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of a compound that modulates the activity of N-kinase to any of the above mentioned sites can be achieved by direct injection of the compound that modulates the activity of N-kinase formulation or by the use of infusion pumps. For injection, the compound that modulates the activity of N-kinase formulation of the invention can be formulated in liquid solutions, preferably in physiologically compatible buffers such as Hank's solution or Ringer's solution. In addition, the compound that modulates the activity of N-kinase formulation may be formulated in solid form and re-dissolved or suspended immediately prior to use. Lyophilized forms are also included. The injection can be, for example, in the form of a bolus injection or continuous infusion (e.g., using infusion pumps) of the compound that modulates the activity of N-kinase formulation.

In one embodiment of the invention, the compound that modulates the activity of N-kinase formulation is administered by lateral cerebro ventricular injection into the brain of a subject, preferably within 100 hours of when an injury (resulting in a condition characterized by aberrant axonal outgrowth of central nervous system neurons) occurs (e.g., within 6, 12, or 24 hours of the time of the injury). The injection can be made, for example, through a burr hole made in the subject's skull. In another embodiment, the formulation is administered through a surgically inserted shunt into the cerebral ventricle of a subject, preferably within 100 hours of when an injury occurs (e.g., within 6, 12 or 24 hours of the time of the injury). For example, the injection can be made into the lateral ventricles, which are larger, even though injection into the third and fourth smaller ventricles can also be made. In yet another embodiment, the compound that modulates the activity of N-kinase formulation is administered by injection into the cisterna magna, or lumbar area of a subject, preferably within 100 hours of when an injury occurs (e.g., within 6, 12, or 24 hours of the time of the injury).

In another embodiment of the invention, the compound that modulates the activity of N-kinase formulation is administered to a subject at the site of injury, preferably within 100 hours of when an injury occurs (e.g., within 6, 12, or 24 hours of the time of the injury).

Duration and Levels of administration

In a preferred embodiment of the method of the invention, the compound that modulates the activity of N-kinase, or analog thereof, is contacted with CNS neurons for an extended period of time to effect modulation of axonal outgrowth. Sustained contact with the compound that modulates the activity of N-kinase, or analog, can be achieved by, for example, repeated administration of the compound that modulates the activity of N-kinase or analog over a period of time, such as one week, several weeks, one month or longer. More preferably, the pharmaceutically acceptable formulation used to administer the compound that modulates the activity of N-kinase, or analog, provides sustained delivery, e.g., "slow release" of the compound that modulates the activity of N-kinase, or analog, to a subject. For example, the formulation may deliver the compound that modulates the activity of N-kinase, or analog, for at least one, two, three, or four weeks after the pharmaceutically acceptable formulation is administered to the subject. Preferably, a subject to be treated in accordance with the present invention is treated with the compound that modulates the activity of N-kinase, or analog, for at least 30 days (either by repeated administration or by use of a sustained delivery system, or both).

As used herein, the term "sustained delivery" is intended to include continual delivery of a compound that modulates the activity of N-kinase or analogue thereof in vivo over a period of time following administration, preferably at least several days, a week, several weeks, one month or longer. Sustained delivery of the compound that modulates the activity of N-kinase or analogue thereof can be demonstrated by, for example, the continued therapeutic effect of the compound that modulates the activity of N-kinase or analogue thereof over time (e.g., sustained delivery of the compound that modulates the activity of N-kinase or analogue thereof can be demonstrated by continued outgrowth or by continued inhibition of outgrowth of CNS neurons over time). Alternatively, sustained delivery of the compound that modulates the activity of N-kinase or analogue thereof may be demonstrated by detecting the presence of the compound that modulates the activity of N-kinase or analogue thereof in vivo over time.

Preferred approaches for sustained delivery include use of a polymeric capsule or a minipump to deliver the formulation. Polymeric capsules can be prepared as described herein. Implantable infusion pump systems (e.g., Infusaid; see e.g., Zierski, J. et al. (1988) *Acta Neurochem. Suppl.*

43:94–99; Kanoff, R. B. (1994) *J. Am. Osteopath. Assoc.* 94:487–493) and osmotic pumps (sold by Alza Corporation) are available in the art. Another mode of administration is via an implantable, externally programmable infusion pump. Suitable infusion pump systems and reservoir systems are also described in U.S. Pat. No. 5,368,562 by Blomquist and U.S. Pat. No. 4,731,058 by Doan, developed by Pharmacia Deltec Inc.

The pharmaceutical formulation, used in the method of the invention, contains a therapeutically effective amount of the compound that modulates the activity of N-kinase or analogue thereof. A "therapeutically effective amount" refers to an amount effective, at dosages and for periods of time necessary, to achieve the desired result. A therapeutically effective amount of the compound that modulates the activity of N-kinase or analogue thereof may vary according to factors such as the disease state, age, and weight of the subject, and the ability of the compound that modulates the activity of N-kinase or analogue thereof (alone or in combination with one or more other agents) to elicit a desired response in the subject. Dosage regimens may be adjusted to provide the optimum therapeutic response. A therapeutically effective amount is also one in which any toxic or detrimental effects of the compound that modulates the activity of N-kinase or analogue thereof are outweighed by the therapeutically beneficial effects. A non-limiting dosage range is about 5 μM –1000 μM, although the particular optimal dosage will vary depending upon, among other factors, the particular compound that modulates the activity of N-kinase, or analogue thereof, used.

It is to be noted that dosage values may vary with the severity of the condition to be alleviated. It is to be further understood that for any particular subject, specific dosage regimens should be adjusted over time according to the individual need and the professional judgment of the person administering or supervising the administration of the compound that modulates the activity of N-kinase or analogue thereof and that dosage ranges set forth herein are exemplary only and are not intended to limit the scope or practice of the claimed invention.

The invention, in another embodiment, provides a pharmaceutical composition consisting essentially of a compound that modulates the activity of N-kinase and a pharmaceutically acceptable carrier, as well as methods of use thereof to modulate axonal outgrowth by contacting CNS neurons with the composition. By the term "consisting essentially of" is meant that the pharmaceutical composition does not contain any other modulators of neuronal growth such as, for example, nerve growth factor (NGF). In one embodiment, the pharmaceutical composition of the invention can be provided as a packaged formulation. The packaged formulation may include a pharmaceutical composition of the invention in a container and printed instructions for administration of the composition for treating a subject having a disorder associated with an injury of central nervous system neurons, e.g., an injury to retinal ganglion cells, a spinal cord injury or a traumatic brain injury. Use of the compound that modulates the activity of N-kinases, and analogues thereof, of the invention in the manufacture of a medicament for modulating the outgrowth of CNS neurons (e.g., mammalian CNS neurons) is also encompassed by the invention.

In vitro Treatment of CNS Neurons

CNS neurons can further be contacted with a compound that modulates the activity of N-kinase, in vitro to modulate axonal outgrowth in vitro. Accordingly, CNS neuron cells can be isolated from a subject and grown in vitro, using techniques well known in the art, and then treated in accordance with the present invention to modulate axonal outgrowth. Briefly, a CNS neuron cell culture can be obtained by allowing neuron cells to migrate out of fragments of neural tissue adhering to a suitable substrate (e.g., a culture dish) or by disaggregating the tissue, e.g., mechanically or enzymatically, to produce a suspension of CNS neuron cells. For example, the enzymes trypsin, collagenase, elastase, hyaluronidase, DNase, pronase, dispase, or various combinations thereof can be used. Trypsin and pronase give the most complete disaggregation but may damage the cells. Collagenase and dispase give a less complete dissagregation but are less harmful. Methods for isolating tissue (e.g., neural tissue) and the disaggregation of tissue to obtain cells (e.g., CNS neuron cells) are described in Freshney R. I., Culture of Animal Cells, A Manual of Basic Technique, Third Edition, 1994, the contents of which are incorporated herein by reference.

Such cells can be subsequently contacted with a compound that modulates the activity of N-kinase in amounts and for a duration of time as described above. Once modulation of axonal outgrowth has been achieved in the CNS neuron cells, these cells can be re-administered to the subject, e.g., by implantation. It is preferred that the cells are not allowed to differentiate extensively in vitro, as cells that integrate most successfully in a subject are primitive cells.

The invention is further illustrated by the following examples, which should not be construed as further limiting. The contents of all references, patents and published patent applications cited throughout this application, as well as the Figures and the Sequence Listing are hereby incorporated by reference.

EXAMPLES

Example I

Isolation and Characterization of the N-kinase Polypeptide

Neocortical gray matter from bovine brain was homogenized in buffer containing protease and phosphatase inhibitors, and particulate material was centrifuged down. The soluble fraction from approximately 1 kg of tissue was used as the starting material for isolation of the kinase.

During the purification process, kinase activity was monitored using an in-gel kinase method. In this method, a histone HF-1 substrate protein is polymerized into a 10% polyacrylamide gel before the samples to be analyzed are electrophoresed in the gel. Following completion of the electrophoresis, proteins are partially renatured with guanidium isothiocyanate and incubated in the presence [$^{32}$P]-ATP plus $Mn^{2+}$, with or without 6-TG present. (Activation by $Mn^{2+}$, but not by $Mg^{2+}$ or $Ca^{2+}$, is a distinctive property of N-kinase). The purification of the kinase was monitored by looking for a 6-TG-inhibitable radioactive band corresponding to the site where the kinase phosphorylates the HF-1 substrate in the gel.

In the first step of the purification process the starting material was subjected to cation-exchange chromatography (using a Fast-S column, Pharmacia). A 6-TG inhibitable kinase activity bound strongly to this column and eluted with 0.3 M NaCl. The cation-exchange column fraction containing N-kinase was subsequently separated on a Cibacron Blue column (Pharmacia), which allows for the separation of adenine nucleotide-binding proteins. A 6-TG inhibitable, 47–50 kDa polypeptide bound strongly and required a NaCl concentration of 1.5 M NaCl for elution (see FIG. 1A).

Figure 1:
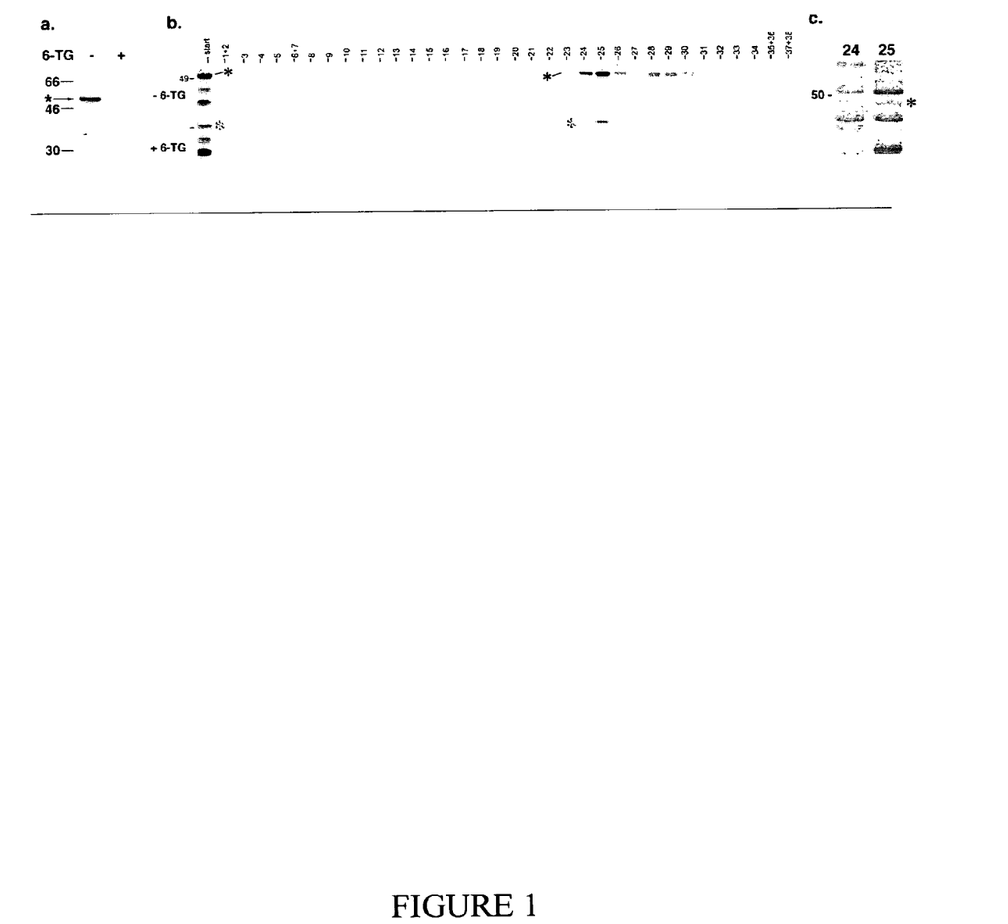

The eluted fraction containing the N-kinase polypeptide was, then, subjected to reversed-phase chromatography with a C4 hydrophobic interaction column (Pharmacia). Briefly, the Cibacron Blue column fraction containing the N-kinase was applied to the C4 column and eluted with a gradient of increasing acetonitrile-isopropanol concentration. Evaluation of the kinase activity of the column fractions by in-gel kinase assays showed that the 6-TG-inhibitable, HF-1-phosphorylating activity eluted in fractions 24–26 (FIG. 1B). To achieve a higher level of purification, these fractions were pooled, re-applied to the same column, and the separation was repeated with a gradient of increasing acetonitrile-isopropanol concentration. The N-kinase polypeptide, again, eluted at fractions 24–26.

The column fractions containing the highest concentrations of N-kinase were lyophilized and applied to a 10% polyacrylamide SDS gel. A small portion of the sample was run on a parallel gel to carry out in-gel kinase assays. A band at 49 kDa was clearly visible after staining the gel with Coomassie blue; this coincided in its migration position with the 6-TG-inhibitable kinase activity. This band was cut out and it was verified that it contained HF-1-phosphorylating activity.

The gel band containing the N-kinase polypeptide was then subjected to partial proteolytic digestion, the proteolytic fragments were analyzed by mass spectroscopy and the masses of the fragments compared to those of various known peptides using the process described in, for example, Eng J. K. et al. (1994) *J. Am. Soc. Mass. Spectrom.* 5:976–989; Chittum H. S. et al. (1998) *Biochemistry* 37:10866–870; and LeRoy G. et al. (1998) *Science* 282: 1900–04, the contents of which are incorporated herein by reference.

This analysis revealed that N-kinase is an isoform of MST-3, i.e., either MST-3 itself, MST-3b, or an as yet undefined isoform. These proteins are members of the STE family of serine-threonine kinases that are found throughout the animal kingdom. STE family members are generally components of modular signaling cassettes that are involved in various aspects of cellular differentiation. FIG. 2 depicts the amino acid sequence of the N-kinase. Direct matches between the purified protein and the published sequence are shown in blue. K65 (bold type) lies in the ATP-binding region of the kinase domain.

EQUIVALENTS

Those skilled in the art will recognize, or be able to ascertain using no more than routine experimentation, many equivalents to the specific embodiments of the invention described herein. Such equivalents are intended to be encompassed by the following claims.

---

I claim:

1. An in vitro method of determining if a compound stimulates or inhibits axonal growth of a central nervous system neuron by increasing or decreasing bovine N-kinase dependent phosphorylation of a substrate comprising the steps of:
   a) contacting bovine N-kinase with a test compound;
   b) selecting a test compound that increases or decreases bovine N-kinase dependent phosphorylation of a substrate;
   c) contacting a central nervous system neuron, in vitro, with said selected test compound; and
   d) determining if the compound stimulates or inhibits axonal outgrowth of the central nervous system neuron.

2. An in vitro method of determining if a compound stimulates or inhibits axonal growth of a central nervous system neuron by increasing or decreasing human N-kinase dependent phosphorylation of a substrate comprising the steps of:
   a) contacting human N-kinase with a test compound;
   b) selecting a test compound that increases or decreases N-kinase dependent phosphorylation of a substrate;
   c) contacting a central nervous system neuron, in vitro, with said selected test compound; and
   d) determining if the compound stimulates or inhibits axonal outgrowth of the central nervous system neuron.

3. The method of claim 2, wherein human N-kinase is recombinantly produced.

4. The method of claim 2, wherein the test compound decreases human N-kinase dependent phosphorylation of the substrate.

5. The method of claim 2, wherein the lest compound increases human N-kinase dependent phosphorylation of the substrate.

* * * * *

SEQUENCE LISTING

<160> NUMBER OF SEQ ID NOS: 1

<210> SEQ ID NO 1
<211> LENGTH: 272
<212> TYPE: PRT
<213> ORGANISM: Homo sapiens

<400> SEQUENCE: 1

```
Met Asp Ser Arg Ala Trp Gly Ala Asn Lys Arg Arg Ala Thr His Gly
1               5                   10                  15

Gly Ser Thr Asn Lys Ala Asp Thr Lys Lys Gly Lys Gly Ser Gly Val
            20                  25                  30

Lys Gly Asp Asn Arg Thr Lys Val Val Ala Lys Asp Ala Asp Asp Thr
        35                  40                  45

Val Ser Cys Asp Ser Tyr Val Thr Lys Tyr Tyr Gly Ser Tyr Lys Asp
    50                  55                  60

Thr Lys Trp Met Tyr Gly Gly Ser Ala Asp Gly Asp Thr Ala Thr
65                  70                  75                  80

Arg Lys Gly Asp Tyr His Ser Lys Lys His Arg Asp Lys Ala Ala Asn
                85                  90                  95

Val Ser His Gly Val Lys Ala Asp Gly Val Ala Gly Thr Asp Thr Lys
            100                 105                 110

Arg Asn Thr Val Gly Thr Trp Met Ala Val Lys Ser Ala Tyr Asp Ser
        115                 120                 125

Lys Ala Asp Trp Ser Gly Thr Ala Ala Arg Gly His Ser His Met Lys
    130                 135                 140

Val Lys Asn Asn Thr Gly Asn Tyr Ser Lys Lys Val Ala Cys Asn Lys
145                 150                 155                 160
```

-continued

```
Ser Arg Thr Ala Lys Lys His Lys Arg Asn Ala Lys Lys Thr Ser Tyr
            165                 170                 175

Thr Asp Arg Tyr Lys Arg Trp Lys Ala Ser His Asp Asp Ser Ser Ser
            180                 185                 190

Asp Ser Asp Ala Thr Asp Gly Ala Ser Gly Gly Ser Asp Ser Gly Asp
            195                 200                 205

Trp Thr Arg Lys Asp Lys Asn Asn Gly Ala Ser Asp Asp Arg Asn Lys
            210                 215                 220

Met Lys Asp Lys Arg Ser Cys Ser Thr Ser Ala Lys Lys Ser Ala Cys
225             230                 235                 240

Gly Gly Asn Gly Ser Arg Gly Ala Tyr Ala Ala Cys Gly Ser Asp Thr
            245                 250                 255

Met Val Ala Val Arg Arg Tyr Ser Ser Gly Gly Gly Thr Ser Ser His
            260                 265                 270
```